US008906630B2

(12) United States Patent
Weiser et al.

(10) Patent No.: US 8,906,630 B2
(45) Date of Patent: Dec. 9, 2014

(54) ASSAYS FOR DETECTING PATHOGENIC RESPIRATORY BACTERIA

(75) Inventors: Jeffrey N. Weiser, Merion, PA (US); Jane M. Gould, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1182 days.

(21) Appl. No.: 11/065,906

(22) Filed: Feb. 25, 2005

(65) Prior Publication Data

US 2005/0233395 A1    Oct. 20, 2005

Related U.S. Application Data

(60) Provisional application No. 60/548,328, filed on Feb. 27, 2004.

(51) Int. Cl.
| | | |
|---|---|---|
| G01N 33/53 | (2006.01) | |
| A61K 39/02 | (2006.01) | |
| A61K 39/09 | (2006.01) | |
| G01N 33/569 | (2006.01) | |

(52) U.S. Cl.
CPC ...... *G01N 33/56911* (2013.01); *G01N 2800/12* (2013.01); *G01N 2333/4737* (2013.01)
USPC ....... 435/7.1; 435/7.32; 435/7.34; 424/184.1; 424/234.1; 424/244.1; 424/246.1; 424/249.1; 424/256.1; 424/260.1; 424/264.1

(58) Field of Classification Search
USPC .......... 424/130.1, 150.1, 163.1, 164.1, 184.1; 435/4, 7.1, 7.2, 7.32, 7.34, 7.92, 7.94, 435/34, 39, 174, 243, 286.3, 287.1, 287.2; 436/501, 513, 536, 540
See application file for complete search history.

(56) References Cited

U.S. PATENT DOCUMENTS 5,358,852 A * 10/1994 Wu .............................. 435/7.94

FOREIGN PATENT DOCUMENTS

EP            1076240      *  2/2001  ............. G01N 33/53

OTHER PUBLICATIONS

Homlberg et al. 1085. J. of Clinical Micrbio. vol. 22(1): 111-115.*
Gillespie et al., (1994. J. Clin. Pathol. vol. 47:749-751).*
Holmberg et al., (1985. J. of Clin. Microb. vol. 22(1 ): 111-115).*
Christodoulides et al., (Anal. Chem. 2002. vol. 74:3030-3036).*
Cole et al., Infect. Immun., 67:3267-3275, 1999.*
Bird, R.E., Hardman, K.D., Jacobson, J.W., Johnson, S., Kaufman, B.M., Lee, S.M., Lee, T., Pope, S.H., Riordan, G.S., and Whitlow, M., "Single-Chain Antigen-Binding Proteins," Science 242:423-426 (1988).
Claus, D.R., Osmand, A.P., and Gewurz, H., "Radioimmunoassay of Human C-Reactive Portein and Levels in Normal Sera," J. Lab. Clin. Med. 87:120-128 (1976).
Cole, A.M., Dewan, P., and Ganz, T., "Innate Antimicrobial Activity of Nasal Secretions," Infect. Immun. 67(7):3267-3275 (1999).
Gerwurz, H., Zhang, X.H., and Lint, T.F., "Structure and Function of the Pentraxins," Curr. Opin. Immunol. 7:54-64 (1995).
Gillman, S., Smith, G., "Site-Specific Mutagenesis Using Synthetic Oligodeoxyribonucleotide Primers: I. Optimum Conditions and Minimum Oligodeoxyribonucleotide Length," Gene 8:81-97 (1979).
Gould, J., and Weiser, J.N., "Expression of C-Reactive Protein in the Human Respiratory Tract," Infect. Immun. 69(3):1747-1754 (2001).
Gu, J., Liu, Y., Zia, L., Wan., H., Li, P., Zhang, X., and Ruan, C., "Construction and Expression of Mouse-Human Chimeric Antibody SZ-5I Specific for Activated Platelet P-Selectin," Thrombosis and Haemostasis 77(4):755-759 (1997).
Harlow, E., and Lane, D., "Antibodies: A Laboratory Manual," Cold Spring Harbor Laboratory Press, N.Y. (1989).
Harlow, E., and Lane, D., "Using Antibodies: A Laboratory Manuil," Cold Spring Harbor Laboratory Press, NY (1999).
Houston, J.S., Levinson, D., Mudgett-Hunter, M., Tai, M.S., Novotny, J., Margolies, M.N., Ridge, R.J., Bruccoleri, R.E., Haber, E. Crea, R., and Oppermann, H., "Protein Engineering of Antibody Binding Sites: Recovery of Specific Activity in an Anti-Digoxin Single-Chain Fv Analogue Produced in *Escherichia coli*," Proc. Natl. Acad. Sci. USA 85:5879-588 (1988).
Kaliner, M.A., "Human Nasal Respiratory Secretions and Host Defense," Am. Rev. Respir. Dis. 144:S52-56 (1991).
Lysenko, E.S., Gould, J., Bals, R., Wilson, J.M., and Weiser, J.N., "Bacterial Phosphorylcholine Decreases Susceptibility to the Antimicrobial Peptide LL-37/hCAP18 Expressed in the Upper Respiratory Tract," Infect. Immun. 68(3):1664-1671 (2000).
Marks, J.D., Hoogenboom, H.R., Bonnert, T.P., McCafferty, J., Griffiths, A.D., and Winter, G., "By-Passing Immunization Human Antibodies from V-gene Libraries Displayed on Phage," J. Mol. Biol. 222:581-597 (1991).
Mosser, J.L., and Tomasz, A., "Choline-containing Teichoic Acid as a Structural Component of Pneumococcal Cell Wall and Its Role in Sensitivity to Lysis by an Autolytic Enzyme," J. Biol. Chem. 245:287-298 ((1970).
Pepys, M.B., and Baltz, M.L., "Acute Phase Proteins with Special Reference to C-Reactive Protein and Related Proteins (Pentaxins) and Serum Amyloid A Protein," Adv. Immunol. 34:141 (1983).

(Continued)

*Primary Examiner* — Rodney P Swartz
(74) *Attorney, Agent, or Firm* — Mark S. Cohen; Pearl Cohen Zedek Latzer Baratz LLP

(57) ABSTRACT

The present invention encompasses methods, assays and kits for the detection of pathogenic bacteria in a patient and for the differential diagnosis of pulmonary diseases associated with pathogenic bacteria from pulmonary diseases not associated with pathogenic bacteria.

11 Claims, 4 Drawing Sheets

(56) References Cited

OTHER PUBLICATIONS

Pepys, M.B., Baltz, M., Gomer, D., Davies, A.J.S., and Doenhoff, M., "Serum Amyloid P-Component is an Acute-Phase Reactant in the Mouse," Nature 278:259-261 (1979).

Roberts, S., Cheetham, J.C., and Rees, A.R., "Generation of an Antibody with Enhanced Affinity and Specificity for its Antigen by Protein Engineering," Nature, 328:731-734 (1987).

Szalai, A.J., Agrawal, A., Greenhough, T.J., and Volanakis, J.E., "C-Reactive Protein: Structural Biology, Gene Expression, and Host Defense Function," Immunol. Res. 16:127-136 (1997).

Szalai, A.J., Briles, D.E., and Volanakis, J.E., "Human C-Reactive Protein is Protective Against Fatal *Streptococcus peumoniae* Infection in Transgenic Mice," J. Immunol. 155:2557-2563 (1995).

Tuszynski, G.P., Rothman, V.L., Murphy, A., Siegler, K. and Knudsen, K.A., "Thrombospondin Promotes Platelet Aggregation," Blood, 72(1):109-115 (1988).

Volanakis, J.E., and Kaplan, M.H., "Specificity of C-Reactive Protein for Choline Phosphate Residues of Pneumococcal C-Polysaccharide," Proc. Soc. Exp. Biol. Med. 136:612-614 (1971).

Weiser, J.N., Pan, N., McGown, K.L., Musher, D., Martin, A., and Richards, J., "Phosphorylcholine on the Lipopolysaccharide of *Haemophilus influenzae* Contributes to Persistence in the Respiratory Tract and Sensitivity to Serum Killing Mediated by C-Reactive Protein," J. Exp. Med. 187(4):631-640 (1998).

Whitehead, A.S., Zahedi, K., Rits, M., Mortensen, R.F., and Lelias, J.M., "Mouse C-Reactive Protein," Biochem. J. 266:283-290 (1990).

Wright, A., Shin, S.U., and Morrison, S.L., "Genetically Engineered Antibodies: Progress and Prospects," Critical Rev. Immunol. 12(3,4):125-168 (1992).

Young, B., Gleeson, M., and Cripps, A.W., "C-Reactive Protein: A Critical Review," Pathology 23:118-124 (1991).

\* cited by examiner

ASSAYS FOR DETECTING PATHOGENIC RESPIRATORY BACTERIA

CROSS-REFERENCE TO RELATED APPLICATIONS

The present application claims priority pursuant to 35 U.S.C. §119(e) to U.S. Provisional Application No. 60/548,328, filed Feb. 27, 2004, which is hereby incorporated by reference in its entirety herein.

GOVERNMENT INTERESTS

This invention was supported in part by the National Institutes of Health Grant No KO8-NIAID-001798. The Government may have certain rights in this invention.

FIELD OF THE INVENTION

The present invention relates to a rapid diagnostic test for determining the class of microorganism causing an infection in a patient with a respiratory infection, thereby permitting strategic clinical intervention.

BACKGROUND OF THE INVENTION

Respiratory tract infections are a leading cause of premature mortality in the US and worldwide. Even upper respiratory infections, such as otitis media and sinusitis can lead to morbidity. Consequently, innate immunity is particularly important component of host defense in the human respiratory tract, particularly in the upper airway which is heavily colonized with a variety of commensal microorganisms, as well as intermittent colonization with known respiratory tract pathogens such as *Streptococcus pneumoniae* and *Haemophilus influenzae* that commonly coexist on the mucosal surface of the nasopharynx. Mediators of host immunity in the human respiratory tract include immunoglobulins A and G, lysozyme, lactoferrin, mucus glycoproteins, secretory leukoprotease inhibitor, secretory phospholipase A, uric acid, peroxidase, aminopeptidase and neutral endopeptidase (Kaliner, *Am. Rev. Respir. Dis.* 144:S52 (1991); Kim & Weiser, "Medical Importance of Normal Microflora," in *Respiratory Infections*, (Tannock, ed.) Thompson Science, London, 1998). As a result, it is often difficult to for healthcare personnel to distinguish between those microorganisms that are causing infection, from those that are simply colonizing the region.

C-reactive protein (CRP) is a known constituent of human sera (Szalai et al., *Immunol. Res.* 16:127-136 (1997)), produced by hepatocytes as a single chain precursor with a cleavable signal sequence at the N-terminus (Weiser et al., *J. Exp. Med.* 187:631-640 (1998)), and induced by proinflammatory cytokines. CRP derives its name from the finding that it binds to the C polysaccharide or cell wall teichoic acid of *Streptococcus pneumoniae*. The concentration of CRP in serum is generally less than 2 µg/ml, but it is known to increase to as much as 1000-fold in response to a stimulus, such as tissue injury or inflammation to levels typically >50 µg/ml (Claus et al., *J. Lab. Clin. Med.* 87:120-128 (1976)). Moreover, the CRP levels are known to decline rapidly when the inflammatory stimulus has been removed with a half-life of ~4-7 hours (Pepys et al., *Adv. Immunol.* 34:141 (1983); Young et al., *Pathology* 23:118 (1991)). As a result, CRP is a recognized clinical marker of the inflammatory process in vivo, although the function of this acute-phase reactant and its precise role in host defense remain poorly understood (Pepys et al., *Nature* 278:259-261 (1979); Whitehead et al., *Biochem. J.* 266:283-290 (1990)).

Mice, which have a constitutively low level of CRP, are resistant to experimental pneumococcal sepsis when carrying the human CRP transgene at levels that would otherwise confer inducible high-levels of expression (Szalai et al., *J. Immunol.* 155:2557-2563 (1996)). Therefore, the use of animal models has been limited because the regulation of CRP in such animals simply does not parallel that of humans.

Human serum CRP is a cyclic pentameric protein (~120 kD), having five, identical, non-covalently bound, non-glycosylated subunits of 206 amino acids, each having a molecular mass of 24 kDa. (Gerwurz et al., *Curr. Opin. Immunol.* 7:54-64 (1995)). CRP binds in a calcium-dependent manner to choline phosphate or phosphorylcholine (ChoP) residues found on C polysaccharide (Volanakis et al., *Proc. Soc. Exp. Biol. Med.* 136:612 (1971)). ChoP is considered to be a highly usual structural feature in prokaryotes. However, in addition to *S. pneumoniae*, many of the bacteria that normally inhabit the human respiratory tract express ChoP, the molecular target of CRP, on their cell surface (Mosser et al., *J. Biol. Chem.* 245:287-298 ((1970)). Found primarily on the mucosal surface of the airway, ChoP has been found on the cell surface of both gram-positive and gram-negative species of bacteria, and it has also been found on *Mollicutes*. More specifically, it is known to be present on the cell surface of certain bacterial pathogens of the human respiratory tract, including *Streptococcus oralis*, *S. mitis*, *Haemophilus influenzae*, *H. somnus*, *Actinobacillus actinomycetemcomitans*, *Pseudomonas aeruginosa*, and *Fusobacterium nucleatum*, as well as certain species of *Actinomyces*, *Neisseria*, such as *N. meningitides*, and *Mycoplasma*, such as *M. fermentans* and *M. pneumoniae*.

However, in an analysis of respiratory tract surface exudates, CRP was not recognized as a component of innate antimicrobial activity (Cole et al., *Infect. Immun.* 67:3267-3275 (1999)), an exclusion that led researchers away from the significance of CRP binding to respiratory pathogens. Although ChoP expression on bacteria has been found to confer resistance to antimicrobial peptides on the mucosa of the upper respirator tract, such as LL-36 and LL-37/hCAP18, that target structural differences in membranes between host and microbial cells (Lysenko et al., *Infect. Immun.* 68:1664-1671 (2000)), only the source and regulation of serum CRP were extensively studied.

The inventors were the first to examine the expression of CPR in the human respiratory tract, particularly in the heavily colonized upper respiratory tract where the organisms bearing the ChoP target reside (Gould & Weiser, *Infect. Immun.* 69(3):1747-1754 (2001)). Using a monoclonal antibody to CRP Gould and Weiser demonstrated that CRP is present in secretions from inflamed (0.17 to 42 µg/ml) and non-inflamed (<0.05 to 0.88 µg/ml) human respiratory tracts in sufficient quantities for an antimicrobial effect. In addition, they reported that the CRP gene was expressed in epithelial cells of the human respiratory tract using in situ hybridization on nasal polyps and reverse transcriptase PCR of pharyngeal cells in culture. However, there is phase variation in the presence or amount of ChoP on the bacterial cell surface in many species expressing this moiety. A direct antimicrobial or bactericidal effect of CRP has been demonstrated only for *H. influenzae* phase variants expressing ChoP in vitro, where concentrations of the protein as low as 20 ng/ml bind to ChoP and mediate a complement-dependent bactericidal effect (Weiser et al., *J. Exp. Med.*, 1998, supra). Nevertheless, this finding only examined CRP in serum, offering no suggestion of direct antimicrobial binding to the pathogens in the respiratory tract.

Current diagnostic tests for respiratory tract infections are slow and often incorrect. The microbiological laboratory evaluation of an adult patient with a presumed respiratory tract infection may include a sputum gram stain, sputum culture and blood culture. Sputum cultures require over 24 hours before the infective organism(s) can be identified. Even then, however, the findings often reflect the patient's diverse oro-pharyngeal colonizing flora, which often may include known pathogens, rather than identify the organism causing the infection. Therefore, because of the high rate of error and lack of specificity, practitioners typically do not bother with sputum gram stains and cultures.

Blood tests are useful to determine microorganisms, if correct, but resolution also requires more than 24 hours of cell culture, and even then may be inaccurate. A blood culture when positive for a microorganism known to cause human respiratory tract infection is very helpful; however, blood cultures are infrequently positive even in the face of impressive radiographic evidence of pneumonia. Moreover, the time needed for cultures to mature in the laboratory can significantly delay establishing a microbiological diagnosis.

Consequently, physicians and healthcare practitioners frequently must rely upon laboratory results based upon current techniques that provide slow, and at best vague and often misleading information. This dilemma leaves the health care practitioner with the need to prognosticate the identity of the microorganism causing the respiratory infection in a patient, based empirically upon what infections are typical in a patient of the same age group with similar co-morbidities in light of the season in which the illness is occurring. The usual clinical scenario, therefore, is one in which the causative microorganism is never identified, and instead of delaying treatment, the patient is simply routinely treated with broad-spectrum antibiotics in the hope of achieving a clinical cure (Kim & Weiser, in *Respiratory Infections*, supra). This empiric usage of antibiotics has led to a serious antimicrobial resistance problem, in both the hospital and outpatient communities. This has been dramatically seen with *Streptococcus pneumoniae*, the most common respiratory tract pathogen in humans, which is increasingly selectively resistant to antibiotic treatment.

Accordingly, until the present invention there has remained a recognized need for a diagnostic test that will quickly and accurately determine the etiology of a respiratory tract infection in a patient to permit specific clinical treatment, as opposed to the frequent use of broad range antibiotics, which over time can induce serious antimicrobial resistance problems in the patient.

SUMMARY OF THE INVENTION

The present invention provides a rapid, reliable and effective diagnostic test to accurately determine the etiology of a respiratory tract infection in a patient, thereby determining the causative microorganism to permit specific clinical treatment. In light of the advantages of the present diagnostic test, healthcare providers will no longer have to resort to the presently used generalized therapy in which broad range antibiotics are frequently immediately administered to the patient, rather than delay the >24 hours needed for cell cultures to develop to permit a definitive diagnosis. Consequently, the use of the present assay not only permits rapid treatment of the patient, thereby averting the infected patient's risk of developing an overwhelming bacterial infection, but the treatment can be focused directly on the specific and identified causative microbe. As a result, the patient need not be exposed to frequent doses of broad-based antibiotics, and therefore, the patient is less likely to develop antimicrobial resistance problems.

The present invention includes a diagnostic assay for identifying a pathogenic respiratory bacteria in a patient, the assay comprising obtaining a biological sample from a patient, contacting a substrate comprising a first antibody that specifically binds C-reactive protein (CRP) with the biological sample, contacting the biological sample with a second antibody that specifically binds the pathogenic respiratory bacteria, and detecting the binding of the second antibody to said pathogenic respiratory bacteria, thereby identifying a pathogenic respiratory bacteria in said patient.

Another object of the present invention is a diagnostic assay for differentially diagnosing a respiratory disease associated with a pathogenic respiratory bacteria from a respiratory disease not associated with a pathogenic respiratory bacteria, the assay comprises, obtaining a biological sample from a patient, contacting the biological sample with a first antibody that specifically binds CRP, contacting the biological sample with a second antibody that specifically binds the first antibody, detecting the binding of the second antibody to said first antibody, and thereby differentially diagnosing a respiratory disease associated with a pathogenic respiratory bacteria from a respiratory disease not associated with a pathogenic respiratory bacteria.

An additional object of the present invention is to provide methods of using the assays to permit treatment of a patient infected by a pathogenic respiratory bacteria, wherein a pathogenic respiratory bacteria causing the infection in a patient is identified permitting identification of an antibiotic that is specific for said identified pathogenic respiratory bacteria.

A further object of the present invention is to provide a kit for identifying a pathogenic respiratory bacteria in a patient using the aforementioned assays.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. For the purpose of illustrating the invention, there are depicted in the drawings certain embodiments of the invention. However, the invention is not limited to the precise arrangements and instrumentalities of the embodiments depicted in the drawings.

FIG. 2A depicts an immunocytochemistry assay of CRP bound to *pneumococcus* and detected with a fluorescent antibody. FIG. 2B depicts an immunocytochemistry assay of an antibody that binds all types of *pneumococcus*. FIG. 2C depicts co-localization of an immunocytochemistry assay of CRP bound to *pneumococcus* and detected with a fluorescent antibody and an antibody that binds all types of *pneumococcus*.

3A depicts an immunocytochemistry assay of CRP bound to *pneumococcus* and detected with a fluorescent antibody. FIG. 3B depicts an immunocytochemistry assay of an antibody that binds all types of *pneumococcus*. FIG. 3C depicts co-localization of an immunocytochemistry assay of CRP bound to *pneumococcus* and detected with a fluorescent antibody and an antibody that binds all types of *pneumococcus*. FIG. 3D shows a gram-stain of the sputum sample depicted in FIGS. 3A through 3C.

FIG. 4A shows immunocytochemistry assay of CRP bound to *pneumococcus* and detected with a fluorescent antibody, demonstrating the *diplococcus* morphology common to *pneumococci*. FIG. 4B is a 1000 fold magnification of FIG. 4A.

Figure 1:
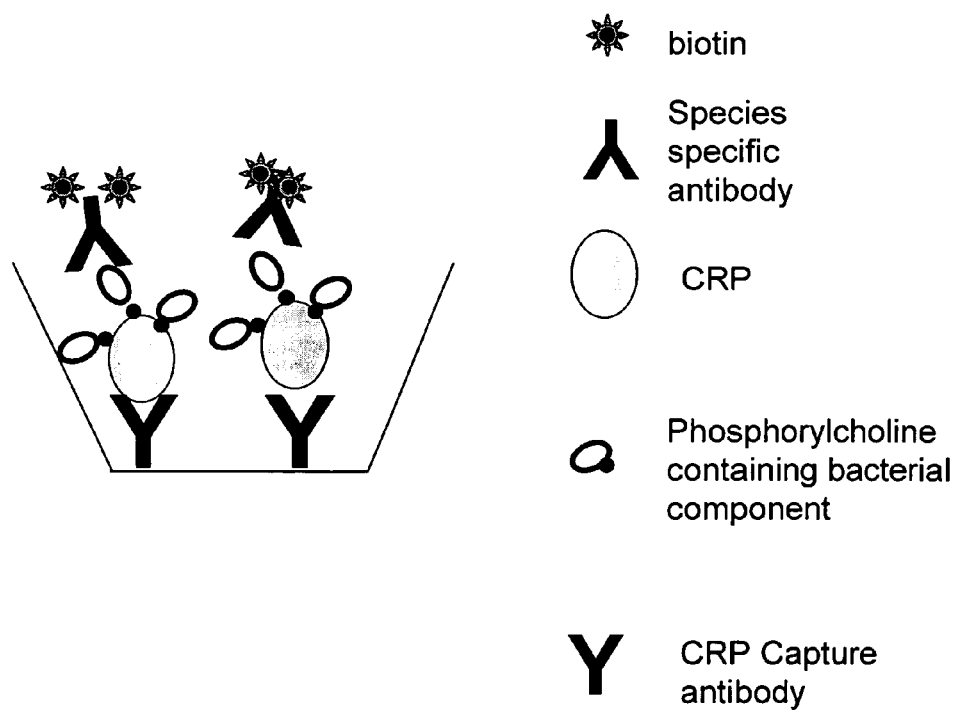
FIG. 1 is a schematic diagram of a capture ELISA.
Figure 2A:
FIGS. 2A-2C depicts the detection of pathogenic bacteria in a biological sample.
Figure 2B:
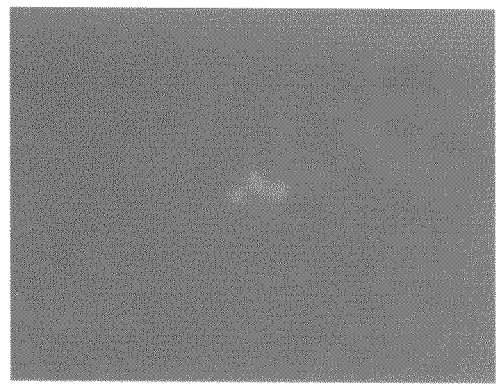
Figure 2C:
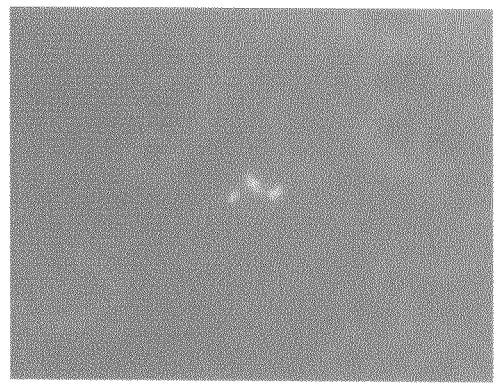
Figure 3A:
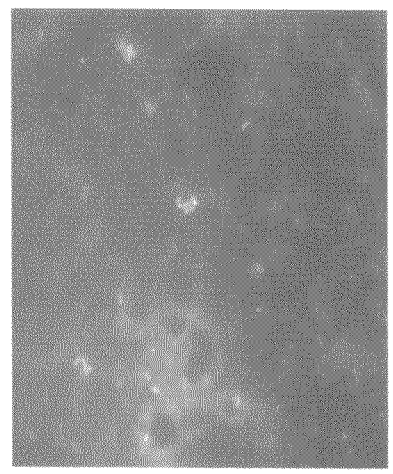
FIGS. 3A-3D depicts the detection of pathogenic bacteria in a sputum sample processed with N-acetyl cysteine. FIG.
Figure 3B:
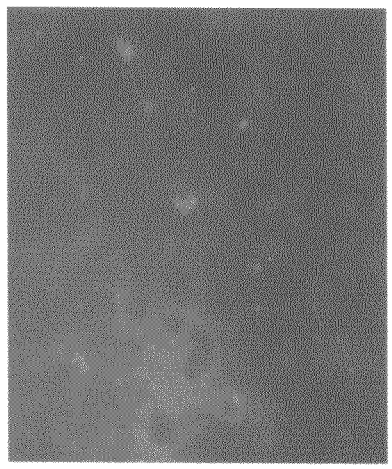
Figure 3C:
Figure 3D:
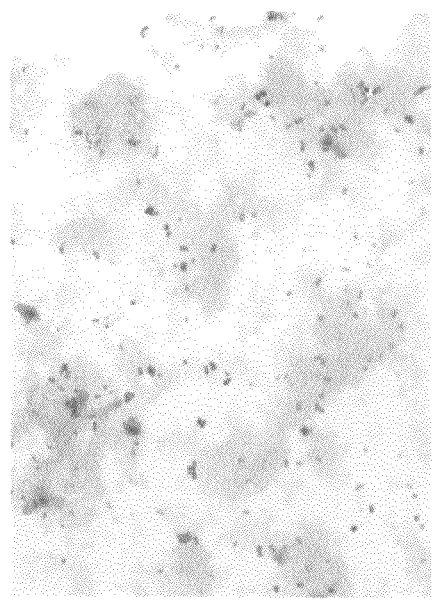
Figure 4A:
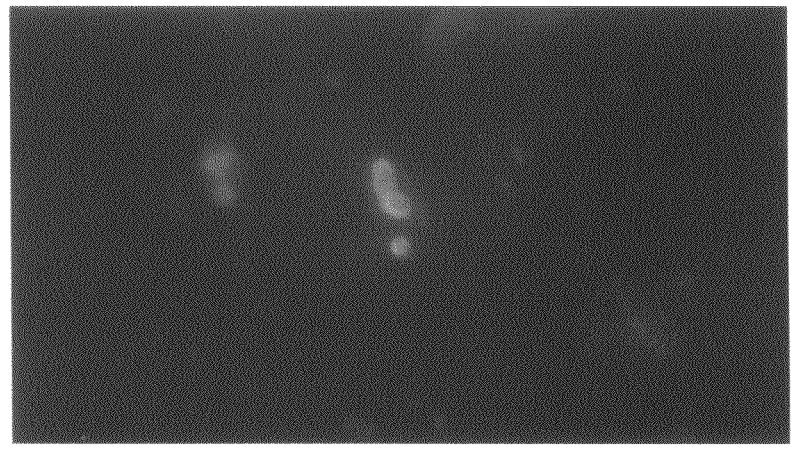
FIGS. 4A-4B depicts the detection of CRP bound to pathogenic bacteria in a sputum sample.
Figure 4B:
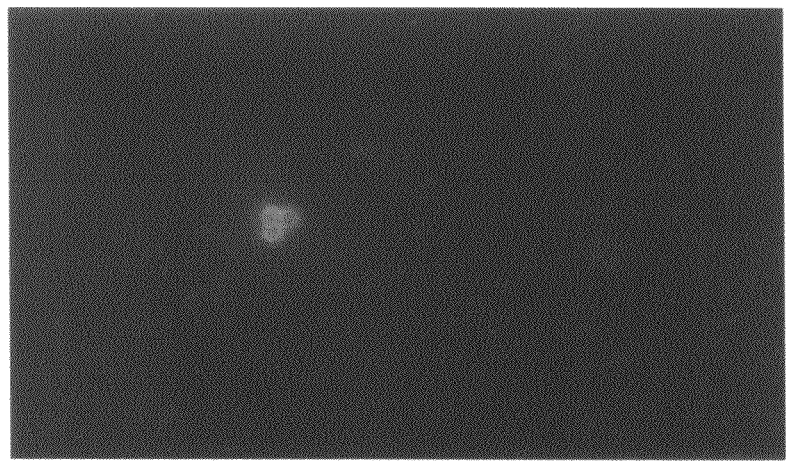

DETAILED DESCRIPTION of CERTAIN EMBODIMENTS of the INVENTION

The present invention encompasses a rapid diagnostic test to determine the class and/or species of microorganisms that are causing an infection in a patient suffering from a bacterial respiratory infection, thereby permitting early and specific clinical treatment of the patient. The present invention is based, in part, on the discovery that C-reactive protein (CRP) specifically binds microorganisms that expresses phosphorylcholine (ChoP). As disclosed herein, CRP is present in the normal human airway in small amounts. However, upon initiation of an infection, CRP specifically binds ChoP expressed on the surface of pathogenic bacteria infecting the human airway. The infection results in an increased concentration of CRP (>1000 fold) in the airway, and an increased level of CRP binding to ChoP. Thus, the present invention provides a method for diagnosing a pathogenic respiratory bacterial infection. The term "pathogenic respiratory bacteria" as used herein, means a prokaryotic bacterial organism that causes a respiratory disease in a mammal.

The present invention provides methods and kits for the diagnosis of pathogenic respiratory bacterial infections in the human airway by detecting the presence of CRP bound to ChoP in a biological sample. "Biological sample," as that term is used herein, means a sample obtained from a mammal that can be used to assess the presence of a pathogenic respiratory bacteria, the level of pathogenic respiratory bacteria present, or both. Such a sample includes, but is not limited to, a blood sample, a spinal fluid sample, a sputum sample, a nasal fluid sample, and a respiratory tract tissue sample. The present invention further provides a method of differentially diagnosing an airway illness that produces increased levels of ChoP, such as a bacterial infection, from other airway illnesses that do not increase levels of ChoP, such as non-bacterial infections, environmental irritants, and the like.

According to the methods of the present invention, pathogenic respiratory bacteria that can be detected using the method of the present invention include, but are not limited to, *Streptococcus pneumoniae, Haemophilus influenzae, Streptococcus oralis, S. mitis, H. somnus, Actinobacillus actinomycetemcomitans, Pseudomonas aeruginosa*, and *Fusobacterium nucleatum*, as well as certain species of *Actinomyces, Neisseria*, such as *N. meningitides*, and *Mycoplasma*, such as *M. fermentans* and *M. pneumoniae*, which are some of the most common causes of acquired respiratory infection in a human.

The present invention further encompasses methods, kits and assays for the detection of any bacteria that expresses ChoP. This is because, as demonstrated herein, CRP binds to ChoP expressed on bacteria, including pathogenic respiratory bacteria. Bacteria detectable according to the methods of the present invention include, but art not limited to, bacteria that infect the spinal fluid, skin, bone, brain, heart, liver, lungs, stomach, kidneys, and other organs of the body. The skilled artisan, armed with the present disclosure and the methods detailed herein, can use the present invention in the detection of any bacteria that expresses ChoP, and in the diagnosis of any disease caused by such bacteria.

As embodied, the present invention comprises collecting a biological sample for determining the presence of a microorganism causing a respiratory infection in a patient, preferably a human. The diagnostic assay of the present invention comprises collecting a biological sample from the patient.

A biological sample is obtained from a human using methods well known in the art, including the collection of sputum sample, airway exudates, airway tissue samples, and other samples. A biological sample for use in the methods of the present invention can further include urine, feces, blood, mucus, lymph fluid, spinal fluid, saliva, serum and tissues other than airway tissues. Preferably the biological sample used in the assay of the present invention is from the respiratory tract, even more preferably from the upper or lower respiratory tract. Examples of biological samples, useful in the assay of the present invention include, but are not limited to, sputum samples, airway exudates, and airway surface fluid (ASF).

The biological sample is processed for use in the methods of the present invention according to standard diagnostic procedures known in the art. As a non-limiting example, a sputum or ASF fluid is collected in an appropriate vessel, such as a sterile specimen vial. The biological sample, preferably a biological sample from the respiratory tract, is solubilized using, for example, acetonitrile to a final concentration of about 60%, trifluoroacetic acid to a final concentration of about 0.1%, or using N-acetyl cysteine according to methods known in the art. Insoluble debris can be removed by centrifugation and neutralized with a buffer, for example, Tris-HCl or other buffers known in the art. Other biological samples used in the present invention are processed according to procedures known to the diagnostician skilled in the art.

The diagnostic assay of the present invention further comprises the use of an antibody to CRP to detect the presence of a pathogenic microorganism infection in a patient. The term "antibody," as used herein, refers to an immunoglobulin molecule which is able to specifically bind to a specific epitope on an antigen. By the term "specifically binds," as used herein, is meant the activity of an antibody which recognizes and binds an epitope of a protein, but does not substantially recognize or bind other molecules in a sample. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As a non-limiting example, a biological sample from a patient, preferably a human, is assayed to detect a pathogenic organism. Assays of the present invention include various immunoassays, for example, immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g. Harlow et al., 1988, Antibodies: A Laboratory Manual, Cold Spring Harbor, N.Y.; Harlow et al., 1999, Using Antibodies: A Laboratory Manual, Cold Spring Harbor Laboratory Press, NY.

Enzyme linked immunoadsorbent assays (ELISA) can be used in the methods, assays and kits of the present invention. In an ELISA assay, proteins or peptides are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological sample to be tested in a manner conducive to immune complex (antigen/antibody) formation. Such conditions preferably include diluting the antisera with diluents such as BSA, bovine gamma globulin (BGG), phosphate buffered saline (PBS)/Tween, and the like. These added agents also tend to assist in the reduction of nonspecific background. The layered antisera is then allowed to incubate for about greater than one hour, at temperatures preferably on the order of about 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing; the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a biotin or peroxidase-conjugated anti-appropriate-animal IgG for a period of time and under conditions which favor the development of immunocomplex formation (e.g., incubation for about 2 hours at room temperature in a PBS-containing solution such as PBS-Tween).

After incubation with the second tagged antibody, and subsequent washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

One skilled in the art would understand, based upon the disclosure provided herein, that an antibody that specifically binds CRP, or an immunogenic portion thereof, and an antibody that specifically binds a pathogenic respiratory bacteria, or an immunogenic portion thereof, is useful in the methods, assay and kits of the present invention. In one embodiment, the antibody specifically binds human CRP. In another embodiment of the present invention, the antibody specifically binds a pathogenic respiratory bacteria. An antibody that specifically binds human CRP is available commercially from, for example, Sigma Chemical Company (St. Louis, Mo.). An antibody that binds a pathogenic respiratory bacteria, or an antigenic component thereof, are available from, for example, Statens Serum Institute (Copenhagen, Denmark).

Antibodies that specifically bind pathogenic respiratory bacteria include, but are not limited to, antibodies that specifically bind each or all of the 90 identified *Streptococcus pneumoniae* serotypes, antibodies that bind *Haemophilus influenzae* type b, antibodies that bind *Haemophilus influenzae* type a, b, c, d, e, f, and antibodies that bind *Streptococcus oralis, S. mitis, Haemophilus, H. somnus, Actinobacillus actinomycetemcomitans, Pseudomonas aeruginosa, Fusobacterium nucleatum, Actinomyces, Neisseria meningitides, Mycoplasma fermentans* and *M. pneumoniae*. Such antibodies are well known in the art, are commercially available, or can be produced using the methods disclosed herein.

Antibodies that specifically bind a pathogenic respiratory bacteria can also bind an antigenic portions thereof, such as a capsule polysaccharides, capsule saccharides, teichoic acid, antigenic proteins, and the like. Such antigenic portions of pathogenic respiratory bacteria are well known in the art.

Antibodies that specifically bind CRP and antibodies that specifically bind a pathogenic respiratory bacteria are well known in the art and include, but are not limited to, monoclonal antibodies, polyclonal antibodies; human antibodies, humanized antibodies, fragments of antibodies, such as Fab fragments, $F(ab)_2$ fragments, Fv fragments, scFv fragment, synthetic antibodies, and the like.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that CRP or a pathogenic respiratory bacteria antigen is rendered immunogenic (e.g., CRP conjugated with keyhole limpet hemocyanin, KLH).

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with CRP or a pathogenic respiratory bacteria antigen.

The antibodies can be produced by immunizing an animal such as, but not limited to, a rabbit or a mouse, with a CRP or a pathogenic respiratory bacteria antigen, or a portion thereof, or by immunizing an animal using a protein comprising at least a portion of CRP or a pathogenic respiratory bacteria antigen, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these proteins can also be used to produce antibodies that specifically bind CRP or a pathogenic respiratory bacteria antigen.

Embodiments of the invention encompass polyclonal, monoclonal, synthetic antibodies, and the like. One skilled in the art would understand, based upon the disclosure provided herein, that the crucial feature of the antibody of the invention is that the antibody bind specifically with CRP or a pathogenic respiratory bacteria antigen. That is, the antibody of the invention recognizes CRP or a pathogenic respiratory bacteria antigen, or a fragment thereof (e.g., an immunogenic portion or antigenic determinant thereof), in an ELISA, a capture ELISA, Western blots, in immunostaining of cells, and immunoprecipitates CRP or a pathogenic respiratory bacteria antigen using standard methods well-known in the art.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al. (1992, Critical Rev. Immunol. 12:125-168), and in the references cited therein, and in Gu et al. (1997, Thrombosis and Hematocyst 77:755-759). The humanized antibodies of the invention have a human framework and have one or more complementarity determining regions (CDRs) from an antibody, typically, but not limited to a mouse antibody, specifically reactive with CRP or a pathogenic respiratory bacteria antigen, or a fragment thereof.

Human constant region (CDR) DNA sequences from a variety of human cells can be isolated in accordance with well known procedures. Preferably, the human constant region DNA sequences are isolated from immortalized B-cells as described in WO 87/02671, which is herein incorporated by reference. CDRs useful in producing the antibodies of the present invention may be similarly derived from DNA encoding monoclonal antibodies capable of binding to CRP or a pathogenic respiratory bacteria antigen. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources, for example, American Type Culture Collection, Manassas, Va.

In addition to the humanized antibodies discussed above, other modifications to native antibody sequences can be readily designed and manufactured utilizing various recombinant DNA techniques well known to those skilled in the art. Moreover, a variety of different human framework regions may be used singly or in combination as a basis for humanizing antibodies directed to CRP or a pathogenic respiratory bacteria antigen. In general, modifications of genes may be readily accomplished using a variety of well-known techniques, such as site-directed mutagenesis (Gillman and Smith, Gene, 8:81-97 (1979); Roberts et al., 1987, Nature, 328:731-734).

The antibodies described herein can be produced using various methods known in the art, including the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The antibodies disclosed herein can also be used in a capture ELISA. Capture ELISAs are well known in the art for reducing background and increasing specificity of detection of an antigen or other molecule. In one embodiment of the present invention, a substrate, such as a polystyrene multi-well plate is coated with an antibody that specifically binds an antigen. As a non-limiting example, the multi-well plate is coated with an antibody that specifically binds CRP. A biological sample, such as solubilized sputum, is then added to the multi-well plate. The antibody specifically binds the antigen, such as CRP, which, as disclosed elsewhere herein, is bound to ChoP on a pathogenic respiratory bacteria. The plate is incubated as disclosed above, and washed as is well known in the art.

The capture ELISA can then be probed with an antibody that specifically binds various pathogenic respiratory bacteria, including, but not limited to, *Streptococcus* species, including *S. oralis, S. mitis, Haemophilus* species, including *H. influenzae, H. somnus, Actinobacillus* species, including *A. actinomycetemcomitans, Pseudomonas* species, including *A. aeruginosa, Fusobacterium* species, including *F. nucleatum, Actinomyces* species, *Neisseria* species, including *N. meningitides*, and *Mycoplasma* species, including *M. fermentans* and *M. pneumoniae*.

The antibody that specifically binds with a pathogenic respiratory bacteria can be labeled and detected using various techniques well known in the art. The detection can be accomplished using techniques described elsewhere herein and known in the art, including, but not limited to, microscopy, colorimetric assays, spectrophotometry, fluorescence, and the like. As demonstrated by the data disclosed herein, the detection of the binding of an antibody that specifically binds a pathogenic respiratory bacteria which is the causative organism of a respiratory disease.

An embodiment of the present invention further encompasses an assay to determine if a respiratory infection is the result of an infection with a bacteria that expresses ChoP and specifically binds CRP. Therefore, according to the methods of the present invention, one of skill in the art can determine if a respiratory infection is due to an infection with, for example, *Streptococcus pneumoniae, S. oralis, S. mitis, Haemophilus influenzae, H. somnus, Actinobacillus actinomycetemcomitans, Pseudomonas aeruginosa, Fusobacterium nucleatum, Actinomyces, Neisseria meningitides, Mycoplasma fermentans, M. pneumoniae,* and the like.

In a preferred embodiment of the present invention, the assay comprises collecting a biological sample from a patient, preferably a human, probing the biological sample with a first antibody that specifically binds CRP, probing the biological sample with a second antibody that specifically binds the first antibody, and detecting the second antibody. The detection of the second antibody is accomplished using methods disclosed elsewhere herein, and well known in the art.

As disclosed elsewhere herein, detection of CRP in a biological sample indicates that the biological sample contains bacteria that express ChoP. Thus, the present invention provides a rapid method for the detection of a bacteria that expresses ChoP.

The antibodies used in the methods, kits and assays of the present invention can be tagged using, for example, chemical tags, metal tags, fluorescent tags, and the like. Tagged antibodies are well known in the art, and include biotin tagged antibodies (detected with strepavidin), radioactivity tagged antibodies, fluorescent tagged antibodies, fluorescein tagged antibodies, FITC-tagged antibodies, Texas Red tagged-antibodies, horseradish peroxidase tagged antibodies, alkaline phosphatase tagged antibodies, gold-tagged antibodies.

An embodiment of the present invention further comprises a diagnostic assay for the differential diagnosis of a disease caused by a pathogenic respiratory bacteria and a disease caused by an environmental factor, such as a non-microbial irritant, or an underlying pulmonary disease, such as asthma, COPD, emphysema, and the like. In other words, as disclosed herein, the present invention provides methods and assays for the detection of CRP binding to ChoP, which is present on pathogenic respiratory bacteria.

In an alternative embodiment, the differential diagnosis assay of the present invention comprises collecting a biological sample from a patient, preferably a human, and processing the biological sample according to methods well known in the art and described elsewhere herein. The sample is assayed according to the methods of the present invention, including ELISAs, capture ELISAs, sandwich assays, radioimmunoassays, and the like. The presence of CRP specifically binding to ChoP in a biological sample is indicative of a pathogenic respiratory bacterial infection, whereas the absence of CRP specifically binding to ChoP in a biological sample is indicative that the pulmonary disease or disorder is not due to a bacterial infection, but is caused by a non-microbial irritant, a microorganism that does not express ChoP, or another underlying pulmonary condition.

The present invention further encompasses methods for diagnosing and/or identifying a pathogenic respiratory in a patient. The method comprises using the diagnostic assay of the present invention to identify a pathogenic respiratory bacteria in a patient, preferably a human. In one embodiment of the present invention, the method comprises obtaining a biological sample from the patient and contacting a substrate comprising a first antibody that specifically binds CRP with the biological sample obtained from the patient. The method further comprises contacting the biological sample with a second antibody that specifically binds the pathogenic respiratory bacteria, or an antigenic portion thereof, such as capsule polysaccharides and teichoic acid, and detecting the binding of the second antibody to the pathogenic respiratory bacteria or an antigenic portion thereof.

Preferably, the methods, kits and assays of the present invention comprise a second antibody that is tagged, as disclosed elsewhere herein. Further, the methods, kits and assays of the present invention are performed as an ELISA, as is well known in the art and described herein.

The present invention further comprises a method for reducing the administration of broad range antibiotics to a patient with a pathogenic respiratory bacterial infection. This is because, as demonstrated by the present disclosure, once the skilled artisan is armed with the assays, methods and kits of the present invention, the skilled artisan can rapidly and accurately diagnose the type of pathogenic respiratory bacteria causing an infection in the respiratory tract. Therefore, the need for broad spectrum antibiotics, which may engender antibiotic resistance if taken improperly, is reduced or eliminated because antibiotics specific for the identified bacteria can be administered.

The method of the present invention comprises employing the diagnostic assay of the present invention to identify a pathogenic respiratory bacteria in a patient. The method comprises obtaining a biological sample from the patient and contacting a substrate comprising a first antibody that specifically binds CRP with the biological sample obtained from the patient. The method further comprises contacting the biological sample with a second antibody that specifically binds the pathogenic respiratory bacteria, or an antigenic portion thereof, and detecting the binding of the second antibody to the pathogenic respiratory bacteria. Once the pathogenic respiratory bacteria has been identified using the assay of the present invention, the skilled artisan can select that appropriate antibiotic for administration to the patient in order to treat the pathogenic respiratory bacterial infection.

The present invention further encompasses various kits for detecting pathogenic respiratory bacteria in a patient. The kits of the present invention comprise an antibody that specifically binds CRP, an antibody that specifically binds a pathogenic respiratory bacteria, and can further comprise a vessel for collecting a biological sample, as well as additional reagents for performing the assays of the present invention which are disclosed elsewhere herein. The kits of the present invention can further comprise instructional materials which describe use of the kit and methods to perform the assays of the present invention. Although model kits are described below, the contents of other useful kits will be apparent to the skilled artisan in light of the present disclosure. Each of these kits is contemplated within the present invention.

In one aspect of the invention, a kit is provided for detecting a pathogenic respiratory bacteria in a biological sample. In one embodiment, the kit comprises an antibody that specifically binds CRP and an antibody that specifically binds a pathogenic respiratory bacteria. For example, the kit comprises at least one, but preferably more than one type of antibody that specifically binds a pathogenic respiratory bacteria. Thus, the kit of the present invention can be used to diagnose the specific bacteria causing a respiratory infection in a patient. The kit further comprises additional reagents for performing the assay of the present invention, including reagents for the detection of secondary antibody binding. The kit is used in the same manner as the methods disclosed herein for the present invention. Additionally, the kit comprises an instructional material for the use of the kit. These instructions simply embody the description and examples provided herein.

In another embodiment, the present invention further comprises a kit for the differential diagnosis of a pulmonary disease caused by a pathogenic respiratory bacteria. In one embodiment, the kit comprises an antibody that specifically binds CRP binding to ChoP. This is because, as disclosed elsewhere herein, CRP binds ChoP expressed on pathogenic respiratory bacteria, but CRP bound to pathogenic respiratory bacterial ChoP is not present in other pulmonary diseases. Thus, the kit of the present invention can be used to differentially diagnose a pathogenic respiratory bacteria causing a respiratory infection in a patient and a non-pathogenic respiratory bacteria pulmonary disease. The kit further comprises additional reagents for performing the assay of the present invention, including reagents for the detection of secondary antibody binding. The kit is used in the same manner as the methods disclosed herein for the present invention. Additionally, the kit comprises an instructional material for the use of the kit. These instructions simply embody the description and examples provided herein.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLES

Example 1

A paraformaldehyde fixed sputum smear obtained from an adult patient with known *Streptococcus pneumoniae* pneumonia was probed using a monoclonal antibody to human CRP followed by a FITC-labeled secondary antibody. Fluorescent microscopy was used to demonstrate that the CRP in the sputum was bound to the *S. pneumoniae* in the sputum. This was then compared to a gram stain of the same smear to confirm the morphology of the microorganism. A second sputum smear from the same patient stained with an isotype control antibody followed by the FITC secondary antibody failed to show any fluorescent staining, demonstrating that the monoclonal antibody to human CRP is specific. The staining technique along with the microscopy work was accomplished in under 2 hours.

Example 2

A biological sample, such as a sputum sample, is obtained from a human patient and processed to solubilize the biological sample. Solubilizing the sample can comprise the addition of acetonitrile to a final concentration of 60% and trifluoroacetic acid to a final concentration of about 0.1% and incubating the sample for about 16 hours at about 25° C. Alternatively, the sample can be solubilized using N-acetyl cysteine according to methods well known in the art. The solubilized sputum sample is then centrifuged at about 1500×g for about 10 minutes to remove particulate and insoluble matter. The sample can then be lyophilized. The sample can then be re-suspended in a physiologically appropriate medium, such as deionized water or saline solution, and sonicated. The acidity of the sample can be neutralized using an appropriate buffer such as Tris-HCl (pH 7.5).

A multi-well plate, preferably polystyrene or another suitable substance, is coated with a dilution of an antibody that specifically binds CRP. Diluting an antibody for an immunoassay is well known in the art and is described elsewhere herein. Diluents include, but are not limited to PBS/Tween, a solution of bovine serum albumin, and the like. The multiwell plate is incubated for a period of time as is well known in the art. The multi-well plate is washed to remove residual antibody and is then ready for addition of the processed biological sample.

The processed biological sample is added to a multi-well plate or other appropriate substrate for an ELISA reaction. The multi-well plate is incubated for an appropriate period of time as disclosed herein. The multi-well plate is then subjected to sequential washes to remove unbound biological sample.

The multi-well plate is then contacted with a second antibody. The second antibody is preferably a tagged antibody that emits a detectable signal upon contact with a stimulus, such as another chemical, light of a certain wavelength, X-ray film, and the like. The second antibody specifically binds a pathogenic respiratory bacteria that expresses ChoP and binds to CRP in the biological sample. The multi-well plate is them subjected to sequential washes to remove the unbound second antibody.

The multi-well plate is then treated to detect the binding of the second antibody to the pathogenic respiratory bacteria. The detection process can comprises the addition of a chemical molecule to the multi-well plate, such as strepavadin. The detection process can also comprise exposing the multi-well plate to a fluorescent or ultraviolet light source in order to cause the tag on the second antibody to emit light at a detectable frequency.

The detection of a signal from the second antibody indicates that a pathogenic respiratory bacteria is present in the biological sample obtained from a patient. The practitioner, once armed with this information can then prescribe or administer an antibiotic or other therapy specific for the pathogenic respiratory bacteria identified by the assay disclosed herein.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A diagnostic assay that detects infection caused by a pathogenic bacteria in the respiratory track airway of a patient, the assay comprising:
   a) contacting a biological sample from the respiratory tract of said patient with a substrate comprising an affixed first antibody that specifically binds C-reactive protein (CRP) bound to a bacteria from said biological sample, wherein said CRP is produced by said patient in the airway in response to infection by said bacteria, wherein said CRP in the sample is bound to phosphorylcholine (ChoP) expressed by said bacteria, and wherein said infection results in an increased concentration of CRP greater than about a thousand fold in the airway of said patient relative to an uninfected patient or a standard;

b) detecting an increased concentration of CRP in said biological sample of said subject relative to the CRP concentration in a biological sample from an uninfected patient or a standard, and detecting an increased concentration of CRP binding to ChoP;

c) contacting the first antibody-bound biological sample with a second antibody that species-specifically binds said bacteria;

d) detecting the binding of the species specific second antibody to said bacteria, wherein said infection is detected when said increased concentration of CRP, and an increased concentration of CRP binding to ChoP is detected;

e) wherein said assay differentiates between pathogenic respiratory bacteria causing a respiratory infection in a patient and a non-pathogenic respiratory bacteria pulmonary disease; and (f) thereby detecting infection caused by said pathogenic bacteria in the airway of said patient.

2. The assay of claim 1, wherein the patient is human.

3. The assay of claim 1, wherein said bacteria is selected from the group consisting of *Streptococcus* species, *S. oralis, S. mitis, Haemophilus* species, *H. influenzae, H. somnus, Actinobacillus* species, *A. actinomycetemcomitans, Pseudomonas* species, *A. aeruginosa, Fusobacterium* species, *F. nucleatum, Actinomyces* species, *Neisseria* species, *N. meningitides, Mycoplasma* species, *M. fermentans* and *M. pneumoniae.*

4. The assay of claim 3, wherein said bacteria is *Streptococcus pneumoniae* or *Haemophilus influenzae.*

5. The assay of claim 1, wherein the biological sample comprises a lower respiratory tract biological sample.

6. The assay of claim 1, wherein the species specific second antibody comprises a tag.

7. The assay of claim 1, wherein the substrate is a multi-well plate.

8. A method of treating a pathogenic bacterial infection in the respiratory track airway of a patient, the method comprising: performing the assay of claim 1; and treating the patient based on the detection of said infection, wherein the treatment step comprises prescribing or administering to the patient an antibiotic that is specific for treating said bacterial infection.

9. The assay of claim 1, wherein the biological sample comprises an upper respiratory tract biological sample.

10. The assay of claim 1, wherein the biological sample comprises secretions from mucosal surfaces of the patient's airway.

11. The assay of claim 1, wherein the biological sample comprises sputum.

* * * * *